United States Patent
Prudhom et al.

(10) Patent No.: US 9,199,896 B2
(45) Date of Patent: Dec. 1, 2015

(54) SYSTEMS AND METHODS OF PRODUCING AROMATIC PRODUCTS

(71) Applicant: UOP LLC, Des Plaines, IL (US)

(72) Inventors: Jon Eric Prudhom, Des Plaines, IL (US); Jason L. Noe, Mount Prospect, IL (US)

(73) Assignee: UOP LLC, Des Plaines, IL (US)

( * ) Notice: Subject to any disclaimer, the term of this patent is extended or adjusted under 35 U.S.C. 154(b) by 289 days.

(21) Appl. No.: 13/954,175

(22) Filed: Jul. 30, 2013

(65) Prior Publication Data

US 2015/0038752 A1  Feb. 5, 2015

(51) Int. Cl.
| | |
|---|---|
| C07C 29/00 | (2006.01) |
| C07C 2/64 | (2006.01) |
| C07C 7/10 | (2006.01) |
| C07C 7/11 | (2006.01) |
| C10G 29/00 | (2006.01) |
| C07C 7/00 | (2006.01) |
| C07C 2/66 | (2006.01) |
| C07C 7/04 | (2006.01) |
| C07C 7/12 | (2006.01) |
| C07C 7/13 | (2006.01) |
| C10G 35/00 | (2006.01) |

(52) U.S. Cl.
CPC . *C07C 7/005* (2013.01); *C07C 2/66* (2013.01); *C07C 7/04* (2013.01); *C07C 7/10* (2013.01); *C07C 7/12* (2013.01); *C07C 7/13* (2013.01); *C10G 35/00* (2013.01)

(58) Field of Classification Search
CPC .............. C07C 2/64; C07C 7/10; C07C 7/11; C10G 29/00
USPC ......... 585/323, 446, 823, 827, 828, 857, 860; 208/133
See application file for complete search history.

(56) References Cited

U.S. PATENT DOCUMENTS

| | | | |
|---|---|---|---|
| 2,713,552 A * | 7/1955 | Lien et al. ..................... | 208/311 |
| 3,742,072 A | 6/1973 | Roth | |
| 7,199,069 B2 | 4/2007 | McLaughlin | |

* cited by examiner

*Primary Examiner* — Thuan D Dang

(57) ABSTRACT

Systems and methods for producing aromatic products are provided. An aromatic stream is provided with aromatic compounds and olefins. The olefins are reacted with aromatic compounds to form colored bodies, and the aromatic stream is distilled to produce an overhead stream and reboiler stream. The colored bodies are in the reboiler stream, and the reboiler stream is passed through an absorbent to remove the colored bodies.

5 Claims, 2 Drawing Sheets

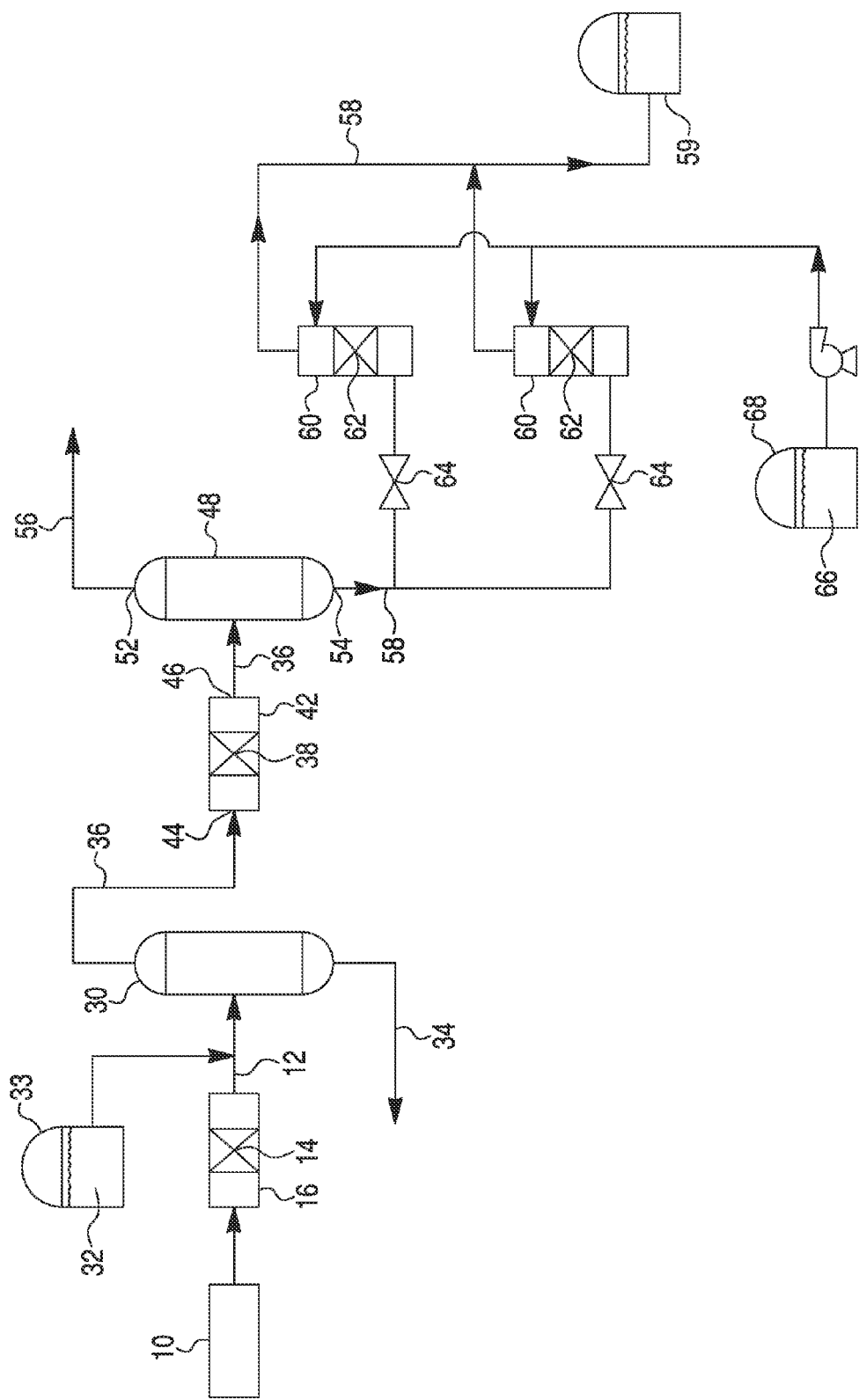

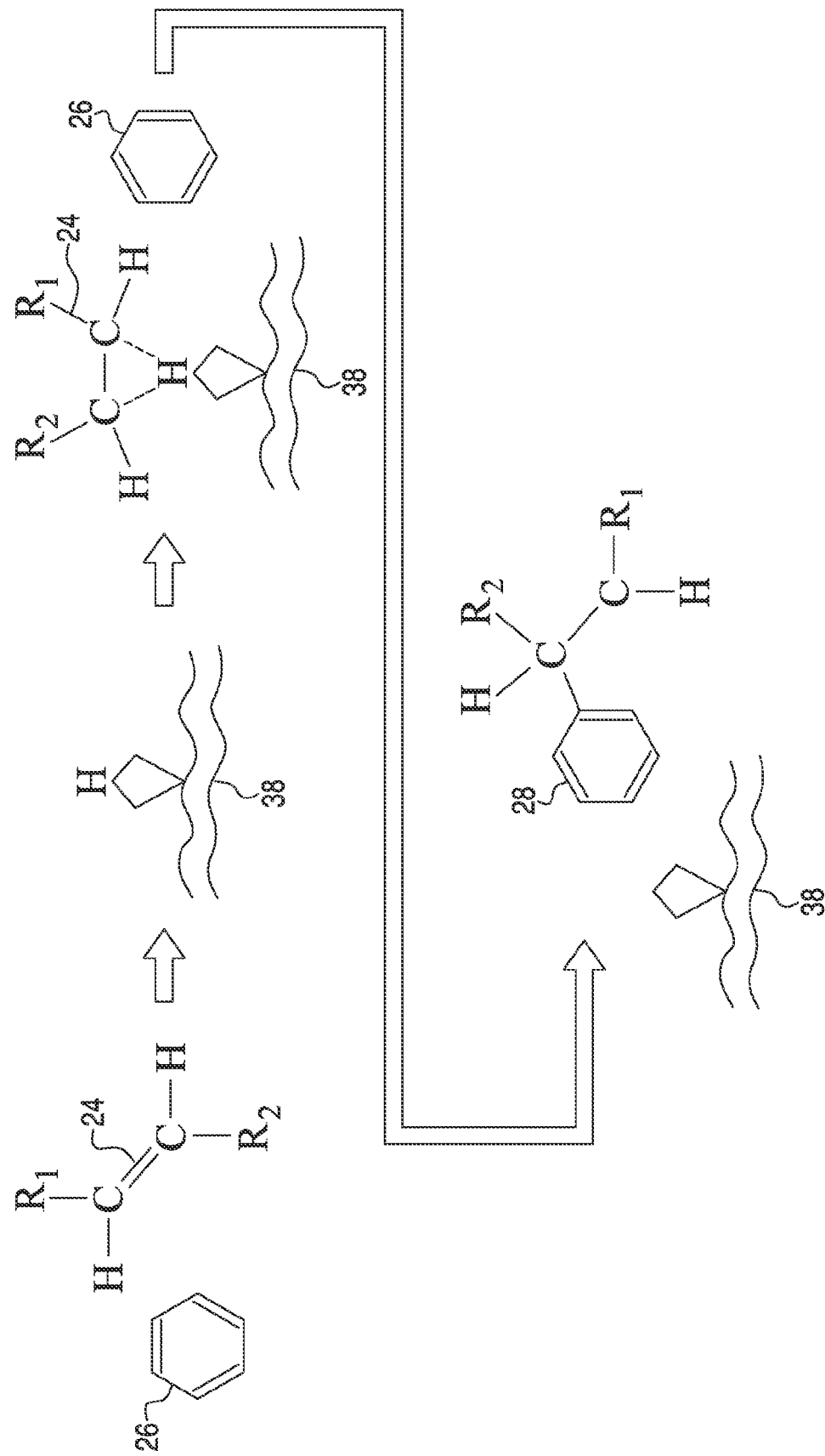

SYSTEMS AND METHODS OF PRODUCING AROMATIC PRODUCTS

TECHNICAL FIELD

The present disclosure generally relates to systems and methods of producing aromatic products. More particularly, the disclosure relates to systems and methods for providing aromatic products and removing impurities from those aromatic products.

BACKGROUND

Crude oil is pumped from wells and transferred to refineries for further processing. Many different molecules are present in the crude oil, and these molecules may be separated into various components that have different ranges of molecular weight and volatility. In one embodiment, the crude oil may be separated into light gases, naphtha, and heavy liquids. The naphtha may be used for a wide variety of purposes, including the production of gasoline for motor vehicles, and the production of several specialty chemicals.

Various aromatic compounds can be produced from the naphtha, such as benzene, toluene, xylene, and other aromatics. Aromatic products primarily contain aromatic compounds, but may include small quantities of other materials such as impurities or additives. The aromatic compounds can be isolated and separately sold for many purposes, including industrial aromatic products that may be used as reactants or solvents. The aromatic products are sold under various specifications that specify various properties of the product, such as purity, color, boiling point, distillation range, percent water, specific gravity, and a wide variety of other properties. Various grades or specifications are available, and products with more stringent specifications tend to sell at higher prices. Isolated and highly purified aromatic products are typically more valuable than gasoline, but sales typically depend on the aromatic products meeting specifications.

Olefins are unsaturated hydrocarbons that are not aromatics, but which do contain one or more double bonds. Olefins are a component of naphtha, and they are undesirable impurities in some aromatic products. One method of removing olefins involves reacting the olefins to produce other products that are more easily removed from the aromatics, but some of these reaction products create colored bodies. A small concentration of colored bodies imparts a noticeable color to an aromatic product, and the color may render the aromatic product out of specification. Separation methods can be used, but separation methods require energy, equipment, and processing time, all of which increase the production cost of the final aromatic product.

Accordingly, it is desirable to provide simple, quick, and inexpensive systems and methods for providing and purifying aromatic products. Furthermore, other desirable features and characteristics of the present application will become apparent from the subsequent detailed description and the appended claims, taken in conjunction with the accompanying drawings and this background.

BRIEF SUMMARY

Methods of producing aromatic products are provided. A method of producing toluene includes processing a feed naphtha stream with a naphtha processing unit to produce a processed naphtha stream. The processed naphtha stream is separated into an aromatic stream and a non-aromatic stream, where the aromatic stream primarily comprises toluene and benzene. Remaining olefins in the aromatic stream are reacted to produce colored bodies, and the aromatic stream is distilled to produce an overhead stream and reboiler stream, where the reboiler stream includes toluene and colored bodies. The colored bodies are removed from the reboiler stream by passing it through an absorbent that selectively absorbs colored bodies over toluene.

In another embodiment, an aromatic stream with aromatic compounds and olefins is provided. The olefins are reacted with aromatic compounds to form colored bodies, and the aromatic stream is distilled to produce an overhead stream and reboiler stream. The colored bodies are in the reboiler stream, and the reboiler stream is passed through an absorbent to remove the colored bodies.

A system of producing aromatic products is also provided. The system includes an olefin removal process unit. An aromatic column is coupled to the olefin removal process outlet, and the aromatic column has an overhead outlet and a reboiler outlet. An absorbent bed is coupled to the reboiler outlet, and the absorbent bed includes an absorbent.

BRIEF DESCRIPTION OF THE DRAWINGS

Various embodiments will hereinafter be described in conjunction with the following figures, wherein like numerals denote like elements, and wherein:

FIG. 1 is a process flow diagram of a system for producing an aromatic product in accordance with one embodiment.

FIG. 2 is a simplified diagram depicting an olefin molecule reacting with an aromatic molecule with the aid of an acid catalyst, where R1 and R2 represent hydrogen or an alkane hydrocarbon chain.

DETAILED DESCRIPTION

The following detailed description is merely exemplary in nature and is not intended to limit the application or uses of the embodiment described. Furthermore, there is no intention to be bound by any theory presented in the preceding technical field, background, brief summary, or the following detailed description.

Naphtha is a product or intermediate produced when crude oil is refined. Naphtha is an intermediate weight product that may boil from about 30 degrees centigrade (° C.) to about 200° C., and includes organic molecules that may vary from about 5 carbons to about 12 carbons. However, different grades of naphtha may have different boiling ranges and different molecular size ranges. Naphtha may be reformed to produce aromatic compounds, olefins, and other molecules, and the aromatic compounds may be separated from the olefins in an extraction process unit. Traces of the olefins remain in the aromatic compounds as an impurity, and these olefins may be reacted with the aromatic products to heavier compounds. Some of the heavier compounds are colored bodies that are heavier than the aromatic compounds. The colored bodies are alkylated aromatics, which have an aromatic component attached to a non-aromatic component. The aromatic compounds may be distilled to separate lighter, lower boiling aromatic compounds from the heavier, higher boiling aromatic compounds, and the colored bodies remain with the heavier, higher boiling aromatics. Reference to "lighter" and "heavier" relates to the relative boiling points of the compounds being distilled, where "lighter" compounds boil at lower temperatures than "heavier" compounds. Low concentrations of the colored bodies may impart a color when present in an aromatic product, and color may make the aromatic products off specification. The colored bodies may be removed from the heavy, higher boiling aromatics with an absorbent that preferentially absorbs colored bodies over aromatic compounds. Absorption may be less expensive than another distillation for separating the colored bodies from the heavier aromatics.

Crude oil refining and specialty chemical processing involve many process steps that can be used at many different points in the overall system. Therefore, a description herein of one processing step following another or coupled to another is intended to include zero, one, or more intervening processing steps. Small differences in crude oil sources or other raw materials can result in different process steps or different orders of process steps. The same raw materials can also be used to make different products, which may involve different process steps, a different order of process steps, or modifications of process conditions. The descriptions herein may not describe every detail or every process step used, but instead is intended to guide those skilled in the art, who understand the process variations and additions which may or may not be needed.

Referring now to FIG. 1, a feed naphtha stream 10 is provided, and the feed naphtha stream 10 may be a component of crude oil or an intermediate or product of crude oil refining. The crude oil can be separated by a distillation technique, and the crude oil may or may not undergo additional processing steps before the distillation. Many different embodiments of the feed naphtha stream 10 are possible, such as heavy naphtha, light naphtha, etc., where the different feed naphtha streams 10 have different components and concentrations of various molecules. Many different types of organic molecules may be in the feed naphtha stream 10, including straight chain alkanes, branched alkanes, alkenes, ringed alkanes, aromatic compounds, alkynes, etc.

The feed naphtha stream 10 may be further processed in a naphtha processing unit 16 to produce a processed naphtha stream 12. Many different types of naphtha processing are possible, including reforming, ethylene production, coke production, and others. FIG. 1 illustrates an embodiment with a reforming reactor as the naphtha processing unit 16, but other types of naphtha processing units 16 could also be used in alternate embodiments. Reforming is a chemical process that changes the molecules in the feed, which is the feed naphtha stream 10 in this case. The reforming process uses a reforming catalyst 14 to re-arrange and restructure the molecules of the feed. Reforming is often used to re-arrange the molecules of the feedstock to produce a higher octane gasoline product, and it may also break some of the feedstock molecules into smaller molecules. Some examples of change from a reforming process include rearranging straight chain alkanes into branched alkanes, converting cyclic alkanes into aromatic compounds such as benzene and toluene, converting alkanes into aromatic compounds, and breaking straight chain alkanes into two or more shorter straight chain alkanes.

Many other changes and modifications are also possible, and the reforming catalyst 14 and process conditions may be adjusted to produce more or less of certain products. For example, in one embodiment the reforming process is set to produce much higher concentrations of benzene and toluene than xylene or heavier aromatics, but in other embodiments the reforming process may be set to produce more xylenes and fewer benzene molecules. The process conditions can also be adjusted to produce more or less aromatic compounds relative to non-aromatic compounds. The reforming process generally produces hydrogen as a by-product, and this hydrogen can be collected and used in other processes. The reforming process also produces olefins, which are non-aromatic organic molecules with a double bond between two carbons. The reforming process may produce light ends, which are small, highly volatile molecules, and the light ends may be vented or removed for separate processing.

In many embodiments, the feed stock is vaporized and pressurized before passing through a bed of the reforming catalyst 14, and the reforming catalyst 14 may be held in one or more reforming reactors (shown as the naphtha processing unit 16) during the reforming process. The feed naphtha stream 10, which may be the feed stock, can be passed through a plurality of reforming reactors, or just one, and the conditions and reforming catalyst 14 may be the same or different in each reforming reactor. Many different modifications or versions of the reforming process are possible, and different versions of the reforming process may be referenced by terms other than reforming, such as platforming.

The processed naphtha stream 12 has aromatic compounds and non-aromatic compounds, including many olefins. In some embodiments, the aromatic and non-aromatic compounds are separated by an extraction process unit 30 that is coupled to the reforming reactor 16. The aromatic and non-aromatic compounds often are miscible and have similar or overlapping boiling points, which makes simple distillation or liquid/liquid separations ineffective. Many of the aromatic and non-aromatic compounds form azeotropes, which further complicates separation by distillation. The aromatic and non-aromatic compounds often have different uses, values, and requirements. For example, the non-aromatics may be valuable as components in gasoline, and gasoline often has a maximum aromatic specification, especially for benzene.

An extraction process unit 30 may be used to separate the aromatic and non-aromatic compounds. In some embodiments, the extraction process unit 30 uses an extraction solvent 32 to aid in the separation. An extraction solvent tank 32 may be directly or indirectly coupled to the extraction process unit 30 to store the extraction solvent 32 for maintenance. However, in other embodiments, solid adsorbents are used to separate the aromatic and non-aromatic compounds. The extraction process unit 30 may use various processes in isolation or in combination, such as extractive distillation, extractive liquid/liquid separation, or selective adsorption, and the operation of the extraction process unit 30 may vary for different feed stocks. Efficient process steps for separating a large quantity of aromatics from a small quantity of non-aromatic compounds will likely be different than efficient process steps for separating a small quantity of aromatics from a large quantity of non-aromatic compounds. The processes and operation of the extraction process unit 30 are often optimized for specific products and product flows.

In some embodiments, the extraction solvent 32 interacts with one component to change its vapor pressure relative to the other, which makes extractive distillations possible. The extraction solvent 32 may also preferentially dissolve one component over the other, such that a miscible mixture of non-aromatic compounds and aromatics forms two separate layers with one type of material combined with the extraction solvent 32 in one layer, and the other material in the other layer. The extraction solvent 32 typically remains with one of the non-aromatic compounds or the aromatics. After the non-aromatic compounds and the aromatics are separated, the extraction solvent 32 may be recovered and re-used, and distillation is a common method of recovery. Therefore, an extraction solvent 32 with a different boiling point than the materials being separated is desired. Some extraction solvents 32 which may be used for separating aromatics from non-aromatics include tetrahydrothiophene 1,1 dioxide (sulfolane), N-methyl pyrrolidone (NMP), N-formyl morpholine (NFM), ethylene glycols, etc.

The extraction process unit 30 produces a non-aromatic stream 34 and an aromatic stream 36, where the non-aromatic stream 34 has relatively few aromatic compounds and the aromatic stream 36 has relatively few non-aromatic compounds, and some of the non-aromatic compounds are olefins. The extraction process unit 30 is not 100 percent efficient, so there are some non-aromatics in the aromatic stream 36 and some aromatics in the non-aromatic stream 34. The non-aromatic stream 34 includes olefin compounds and other non-aromatic compounds, such as alkanes, as well as relatively low concentrations of aromatic compounds. Water may also be present in the aromatic stream 36 and/or the non-aromatic stream 34, and water may be at concentrations up to or even exceeding the saturation point. In some embodiments, the aromatic stream 36 primarily comprises benzene and toluene, and the components and concentrations of the aromatic stream 36 may have been set by the process conditions in the naphtha processing unit 16.

The components of the aromatic stream 36 are typically more valuable if they are separated, and one effective separation technique is distillation. Distillation columns typically separate products based on vapor pressure or boiling point, with the lighter (lower boiling) materials travelling through the distillation column and exiting from the column overhead. The heavier (higher boiling) materials do not travel through the distillation column, and are recovered from the reboiler, which is the bottom portion of the distillation column. Olefins having a similar boiling point to the aromatics may distill over with the lighter aromatic compounds and contaminate the distillation column overhead product. However, olefins having a relatively high boiling point remain in the distillation column reboiler and contaminate the heavy aromatic products recovered from the reboiler.

In one embodiment, the olefins in the aromatic stream 36 are reacted to form a heavy molecule that will remain in a subsequent distillation column reboiler, so the overhead product is essentially free from olefin contamination. An olefin reaction process unit 42 reacts the olefins to produce heavy compounds. In some embodiments, the olefin reaction process unit 42 facilitates a reaction of the bromine reactive species to produce heavy compounds, and olefins are a bromine reactive species. FIG. 1 illustrates the use of an acid catalyst reactor for the olefin reaction process unit 42, but other types of olefin reaction process units 42 could also be used.

The acid catalyst reactor houses an acid catalyst 38, and the acid catalyst 38 facilitates an alkylation reaction between the olefins (and other bromine reactive compounds) and aromatic compounds, as shown in FIG. 2. The acid catalyst 38 facilitates the addition of the olefin 24 to an aromatic compound 26, such as benzene or other aromatics, to produce an alkylated aromatic compound, which is a relatively heavy compound. Some of the alkylated aromatic compounds, which are heavy relative to the aromatic compounds, are colored bodies 28. Many different olefins 24 and aromatic compounds 26 can be combined, so many variations to the embodiment shown in FIG. 2 are possible. In many embodiments, the acid catalyst 38 is clay, and the clay can be acid activated to improve its catalytic performance. However, other acid catalysts 38 may also be used, and the acid catalyst 38 can be customized to very specifically favor certain reactions, such as aromatic alkylation. The molecular weight of the alkylated aromatic compound is higher than either the olefin 24 or the aromatic compound 26 the olefin reacted with, because the two molecules reacted together to form one molecule, and this tends to produce a relatively heavy, high boiling material. In fact, many of the colored bodies 28 and other alkylated aromatic compounds can be so heavy they are tar-like. The relatively high boiling alkylated aromatic compounds tend to remain with the heavier aromatic compounds 26 in a distillation column reboiler, so the overhead product is essentially free from olefins 24 and alkylated aromatic compounds.

Some of the alkylated aromatic compounds are colored bodies 28, similar to a dye, and relatively low concentrations of colored bodies 28 can change the appearance of a product. Many pure aromatic compounds 26 are clear, so it is easy to detect impurities that add color. Low concentrations of colored bodies 28 will change the color of many aromatic products, so low concentrations will often bring an aromatic product out of specification. Therefore, an efficient separation process is desired to remove the colored bodies 28 from the aromatic products. The separation process can also separate the alkylated aromatic compounds that are not colored bodies 28.

Referring back to FIG. 1, the acid catalyst 38 is held in an olefin removal process unit 42, which has an olefin removal process inlet 44 and an olefin removal process outlet 46. The olefin removal process inlet 44 is coupled to the extraction process unit 30 such that the aromatic stream 36 is transferred from the extraction process unit 30 to the olefin removal process unit 42. The olefin removal process outlet 46 may be coupled to an aromatic column 48, so the aromatic stream 36 in the olefin removal process outlet 46 is fed to the aromatic column 48. The aromatic column 48 is a distillation column with an overhead outlet 52 and a reboiler outlet 54.

The aromatic stream 36 exiting the olefin removal process unit 42 is distilled in the aromatic column 48 to produce an overhead stream 56 and a reboiler stream 58. The overhead stream 56 exits the aromatic column 48 from the overhead outlet 52, and the reboiler stream 58 exits the aromatic column 48 from the reboiler outlet 54. The lighter aromatics are separated from the heavier aromatics because lighter compounds travel through the aromatic column 48 to the overhead outlet 52, and heavier compounds do not travel through the aromatic column 48 and exit through the reboiler outlet 54.

In one embodiment, the aromatic compounds 26 in the aromatic stream 36 are primarily benzene and toluene, and the reforming process conditions may have been set for this mix. The benzene is lighter than toluene, so benzene, water, and any other remaining light compounds exit the overhead outlet 54 as the overhead stream 56, and toluene, the colored bodies 28, other alkylated aromatics, and any other heavy compounds exit the reboiler outlet 54 as the reboiler stream 58. The overhead stream 56 is essentially free of olefins 24, because the olefins 24 were converted to colored bodies 28 and other relatively heavy alkylated aromatics. The benzene or other lighter aromatics are also essentially free of colored bodies 28, because the colored bodies 28 exit the aromatic column 48 through the reboiler outlet 54. There may or may not be additional process steps, such as separation of a water layer if present, before the benzene or other overhead stream 56 is sold or otherwise used. In other embodiments, the aromatic stream 36 includes other blends of aromatic compounds 26, such as toluene and xylenes.

In the embodiment described, the reboiler stream 58 includes toluene and the colored bodies 28, as well as the other heavy alkylated aromatics. Toluene is a valuable organic solvent used for many purposes, including paint, paint thinner, silicone sealants, rubber, printing inks, adhesives, leather tanners, and many chemical reactants. Toluene is a raw material for toluene diisocyanate, which is used in the production of polyurethane foam. Toluene is also a raw material for the explosive trinitro toluene, commonly known at TNT. There are other uses for toluene as well, such as a fuel or gasoline octane booster. Relatively low concentrations of colored bodies 28 in the toluene may impart a color, which could be particularly undesirable when toluene is used as a solvent for colored products, such as paint, paint thinner, and inks. Many products that use toluene are marketed with specific colors, such as tanned leather, polyurethane foam, and silicone sealants, so colored toluene may not be acceptable for those products because it could impact the final product color. The production and purification of toluene is one valuable aspect of the systems and methods described herein.

The reboiler stream 56 contains the colored bodies 28, so further processing may be needed to remove color. In one embodiment, the reboiler outlet 54 is coupled to an absorbent bed 60, which has an absorbent 62 inside. The absorbent 62 selectively absorbs colored bodies 28 over toluene or similar aromatic compounds 26, such as xylene, trimethyl benzene, or others. The absorbent 62 removes the colored bodies 28 and other alkylated aromatics, so the reboiler stream 58 is essentially free of colored bodies 28 after passing through the absorbent bed 60. The absorbent 62 may also absorb the alkylated aromatic compounds that are not colored bodies 28, which further increases the purity of the recovered product. After passing through the absorbent bed 60, the reboiler stream 58 can be collected and stored in a reboiler stream storage tank 59 for later use, further processing, or sale.

Absorbent 62 which preferentially absorbs colored bodies 28 over toluene or other similar aromatic compounds 26 are available. For example, activated carbon is used to remove colored bodies 28 from other hydrocarbon streams, and in some embodiments the absorbent 62 is activated carbon. Activated carbon can be processed and/or treated in many different ways to modify the absorption properties, so activated carbon could be acquired that preferentially absorbs larger molecules over toluene or other similar aromatics. Activated carbon and other absorbents 62 which tend to absorb larger molecules are sold commercially. Other possible absorbents 62 include zeolites, alumina, silica gels, or activated clays, and these absorbents can also be processed or treated to absorb larger molecules, or to modify the absorption behavior in other ways.

Some absorbents 62, which may include activated carbon, may absorb water as well as larger molecules. Water is a relatively small molecule, but other factors can influence an absorbent's preferences for different compounds. For example, water is a very polar compound, and the polar nature of water could increase the absorbent's preference for water. Therefore, the absorption bed 60 may be positioned downstream from the reboiler outlet 54, because water is distilled from the reboiler and exits the aromatic column 48 from the overhead outlet 52. The presence of water in the feed to the absorbent bed 60 could hasten the exhaustion of the absorbent 62, because the absorbent 62 may be absorbing both water and colored bodies 28. Therefore, the absorbent 62 may last longer if water is removed before the colored bodies 28 are absorbed. However, it is possible to position the absorbent bed 60 upstream from the aromatic column 48 in some embodiments.

The absorbent 62 will eventually become exhausted, because the available absorption sites will be filled. Various process options are available when the absorbent 62 becomes exhausted. In one embodiment, the exhausted absorbent 62 is discarded and replaced with fresh absorbent 62. The reboiler stream 58 could be stored while the absorbent 62 was replaced, or a plurality of absorbent beds 60 (as illustrated) could be coupled to the reboiler outlet 54 so a fresh absorbent bed 60 could be used while the exhausted absorbent 62 was replaced. A valve 64 could be positioned in the line coupling the reboiler outlet 54 to absorption bed 60 so the absorption bed 60 could be isolated or connected to the reboiler outlet 54 as desired. A plurality of valves 64 used with a plurality of absorption beds 60 would allow isolation of a selected absorption bed 60 for absorbent replacement while another absorption bed 60 was in operation. Alternatively, the reboiler stream 58 could be diverted to another use while the absorbent 62 was replaced, or the aromatic column 48 could be shut down while the absorbent 62 was replaced.

In other embodiments, the absorbent 62 may be regenerated instead of replaced. The colored bodies 28 tend to be heavy, and some may be tar-like, so a liquid regenerant 66 could be passed through the absorbent 62. The liquid regenerant 66 may be used instead of heat for regenerating the absorbent 62 because of the heavy nature of the colored bodies 28 and other absorbed heavy compounds, but heat may useful for absorbent regeneration in some embodiments. The absorbent 62 may preferentially absorb the liquid regenerant 66 over the colored bodies 28, so the colored bodies 28 would be desorbed and replaced by the liquid regenerant 66. In other embodiments, the colored bodies 28 are comparably or preferentially absorbed over the liquid regenerant 66, but sufficient liquid regenerant 66 is passed through the absorbent 62 to desorb and replace the colored bodies 28. The liquid regenerant 66 may then be desorbed from the absorbent, such as with the application of heat to evaporate or boil off the liquid regenerant 66, so the absorbent 62 is reactivated. For example, water could be used as the liquid regenerant 66, and the water could then be removed from the absorbent 62 with heat, but other liquid regenerants 66 could also be used. During absorbent reactivation, the absorbent bed 60 could be isolated from the reboiler outlet 54 using the same process options available for replacing the absorbent 62, as described above.

The liquid regenerant 66 could be stored in a liquid regeneration tank 68 coupled to the absorption bed 60 for the regeneration process. The liquid regenerant 66 could be returned to the liquid regeneration tank 68 for continued use until it was contaminated with an unacceptable concentration of colored bodies 28 or other absorbed materials. Alternatively, the liquid regenerant 66 could be diverted to other processes or disposed of. The absorbent 62 may not need to be regenerated very often, so a temporary, portable regeneration tank 68 could be used, such as a drum or tote bin. The absorbent bed 60 may include steam coils, steam feed lines, electric heating coils, or other components that may aid in regenerating the absorbent 62. Steam or heat may be useful in purging the liquid regenerant 66 from the absorbent 62 after the colored bodies 28 have been desorbed.

After the colored bodies 28 and other alkylated aromatics are removed from the absorbent 62, they may be collected and used for other purposes. For example, the colored bodies 28 and other alkylated aromatics may be used for cutter stock to reduce the viscosity of heavier streams, or they may be used as a solvent for other purposes.

While at least one embodiment has been presented in the foregoing detailed description, it should be appreciated that a vast number of variations exist. It should also be appreciated that the embodiment or embodiments are only examples, and are not intended to limit the scope, applicability, or configuration of the application in any way. Rather, the foregoing detailed description will provide those skilled in the art with a convenient road map for implementing one or more embodiments, it being understood that various changes may be made in the function and arrangement of elements described without departing from the scope as set forth in the appended claims.

The invention claimed is:

1. A method of producing toluene, the method comprising the steps of:
    reforming a feed naphtha stream in a naphtha reforming unit to produce a reformed naphtha stream containing aromatics including benzene, toluene, and olefins
    separating the reformed naphtha stream in an extraction unit with an extraction solvent selected from the group consisting of tetrahydrothiophene 1,1 dioxide (sulfolane), N-methyl pyrrolidone (NMP), N-formyl morpholine (NFM), and ethylene glycols, into an aromatic stream and a non-aromatic stream, wherein the aromatic stream primarily comprises toluene, benzene and olefins;
    alkylating aromatics with olefins in the aromatic stream to produce an alkylation stream containing colored bodies;
    distilling the alkylation stream to produce an overhead stream and a reboiler stream, wherein the reboiler stream comprises toluene and colored bodies; and
    removing the colored bodies from the reboiler stream by passing the reboiler stream through an absorbent bed containing absorbents selected from the group consisting of zeolite, alumina, silica gel, activated clay, activated carbon, or a combination thereof, wherein the absorbent selectively absorbs colored bodies over toluene to produce a stream comprising toluene and essentially free of colored bodies.

2. The method of claim 1, wherein alkylating aromatics with olefins is in the presence of a clay catalyst.

3. The method of claim 1 further comprising regenerating the absorbent.

4. The method of claim 3 wherein regenerating the absorbent further comprises passing a liquid regenerant through the absorbent.

5. The method of claim 1 wherein removing the colored bodies from the reboiler stream further comprises passing the reboiler stream through an absorbent primarily comprising activated carbon.

* * * * *